United States Patent
Boric-Lubecke et al.

(10) Patent No.: US 8,892,189 B2
(45) Date of Patent: Nov. 18, 2014

(54) APPARATUS AND METHOD FOR HEART SIZE MEASUREMENT USING MICROWAVE DOPPLER RADAR

(75) Inventors: Olga Boric-Lubecke, New Providence, NJ (US); Victor Lubecke, New Providence, NJ (US); Katherine A. August, Matawan, NJ (US)

(73) Assignee: Alcatel Lucent, Boulogne-Billancourt (FR)

( * ) Notice: Subject to any disclaimer, the term of this patent is extended or adjusted under 35 U.S.C. 154(b) by 1244 days.

(21) Appl. No.: 10/156,817

(22) Filed: May 30, 2002

(65) Prior Publication Data

US 2004/0015087 A1  Jan. 22, 2004

(51) Int. Cl.
*A61B 5/05* (2006.01)
*A61B 5/00* (2006.01)
*A61B 5/107* (2006.01)

(52) U.S. Cl.
CPC .............. *A61B 5/0507* (2013.01); *A61B 5/6887* (2013.01); *A61B 5/1075* (2013.01); *A61B 5/1076* (2013.01)
USPC .......................................... 600/430; 600/407

(58) Field of Classification Search
USPC .......... 600/407, 437, 443, 425, 429; 324/638, 324/642, 644; 607/101
See application file for complete search history.

(56) References Cited

U.S. PATENT DOCUMENTS

| | | | | |
|---|---|---|---|---|
| 4,332,260 A * | 6/1982 | Bicher et al. | 607/156 |
| 4,344,440 A * | 8/1982 | Aaby et al. | 600/430 |
| 4,397,313 A * | 8/1983 | Vaguine | 607/104 |
| 4,513,748 A * | 4/1985 | Nowogrodzki et al. | 600/453 |
| 4,589,423 A * | 5/1986 | Turner | 607/154 |
| 4,753,243 A * | 6/1988 | Mawhinney et al. | |
| 4,774,961 A * | 10/1988 | Carr | 600/549 |
| 4,991,585 A * | 2/1991 | Mawhinney | 600/430 |
| 5,008,624 A * | 4/1991 | Yoshida | 324/318 |
| 5,101,836 A * | 4/1992 | Lee | 607/155 |
| 5,503,150 A * | 4/1996 | Evans | 600/427 |
| 5,592,939 A * | 1/1997 | Martinelli | 600/424 |
| 5,735,282 A * | 4/1998 | Hossack | 600/458 |
| 5,829,437 A * | 11/1998 | Bridges | 600/430 |
| 5,928,151 A * | 7/1999 | Hossack et al. | 600/443 |
| 5,983,124 A * | 11/1999 | Carr | 600/407 |
| 6,201,989 B1 * | 3/2001 | Whitehead et al. | 600/476 |
| 6,330,479 B1 * | 12/2001 | Stauffer | 607/101 |
| 6,424,597 B1 * | 7/2002 | Bolomey et al. | 367/138 |
| 6,528,994 B2 * | 3/2003 | Suzuki et al. | |
| 6,984,993 B2 * | 1/2006 | Ariav | 324/639 |
| 7,383,076 B2 * | 6/2008 | Ntziachristos et al. | 600/473 |
| 7,591,792 B2 * | 9/2009 | Bouton | 600/587 |
| 2002/0193685 A1 * | 12/2002 | Mate et al. | 600/424 |

* cited by examiner

*Primary Examiner* — Joel Lamprecht
(74) *Attorney, Agent, or Firm* — Harness, Dickey & Pierce

(57) ABSTRACT

An object measurement method and system including an arrangement of individual signal transceivers connected together as a flexible unit. The arrangement of individual signal transceivers measures a characteristic of an object situated within a subject.

9 Claims, 4 Drawing Sheets

APPARATUS AND METHOD FOR HEART SIZE MEASUREMENT USING MICROWAVE DOPPLER RADAR

BACKGROUND OF THE INVENTION

1. Field of the Invention

The present invention generally relates to the non-invasive measurement of an object.

2. Description of Related Art

Ultrasound is a popular non-invasive medical imaging technique. Ultrasound can be used to create an image on a display of a human organ(s) within a human body.

Although ultrasound is very useful, it does have limitations. Foremost, there is a need for direct contact by a transducer probe with the skin in order to generate an image of an organ within the body, which often requires a subject to undress before ultrasound analysis can occur. In addition, it may be difficult to image certain organs if a patient is overweight or very thin.

Magnetic resonance imaging (MRI) devices are another excellent way of imaging organs within the body. However, there are disadvantages. For example, the use of an MRI device to create an image of an organ within the body is relatively expensive. Also, an MRI device may not be used to examine patients with pace makers or other implanted and moveable metal parts.

SUMMARY OF THE INVENTION

The present invention overcomes the disadvantages of prior art non-invasive imaging devices by providing a non-invasive medical imaging device that is easy to use and relatively inexpensive to implement. For example, the non-invasive medical imaging devices according to the embodiment of the present invention do not require a patient to remove his/her clothing before a measuring event takes place. Additionally, the design of the imaging device includes elements that may be obtained easily and at a modest price.

An embodiment of the present invention includes an array of coaxial or waveguide probes connected together as a flexible and semi-rigid formable non-invasive testing device. The connected waveguides or coaxial probes are connected to, or incorporate, wave transmit and receive technology and an output device.

The flexible array of transceivers is used in contact or in close proximity to a subject's body and may be manipulated to conform to the contours of the subject's body. By way of the wave transmit and receive technology, the waveguide or coaxial probes transmit radio-waves, or the like, into the body. Using the Doppler effect of signals transmitted from at least a plurality of the transceivers and signals that reflect off of objects situated within the subject, an image is created on the output device representative of an object(s) within the subject.

DETAILED DESCRIPTION OF THE PREFFERED EMBODIMENTS

Figure 1:
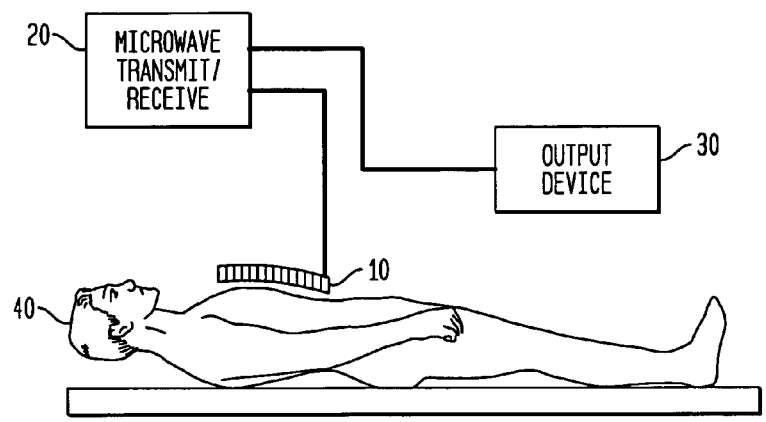
FIG. 1 illustrates in a transceiver array embodiment of the present invention applied to a subject.

FIG. 1 illustrates a transceiver array embodiment of the present invention applied to a subject. As is illustrated in the figure, a transceiver array 10 is positioned on an upper torso area of a subject 40. The transceiver array 10 is flexible, yet it may be formed in a semi-rigid manner to conform to contours of the subject 40. In this case, the transceiver array 10 is formed to the contours of the chest of the subject 40.

The transceiver array 10 is connected to a microwave transmit/receive device 20. The microwave transmit/receive device 20 provides microwave signals to each of the transceiver probes of the transceiver array 10. These microwave signals from the transceiver array 10 enter the subject 40 and reflect off of objects therein. Using each individual transmitted signal from the transceiver array 10 and the respective reflected signals, the Doppler effect is used to create a plot of an object(s) within the subject 40. This plot is then displayed on the output device 30 in two-dimensional form. As an alternative, a plot can be created from signals that reflect off of the surface of the subject 40. For example, movement on the surface of the subject 40 may be plotted using the same Doppler effect technique.

Although the transmit/receive device 20 is described as being a microwave source, it should be understood that the transmit/receive device 20 may utilize any type of coherent, pulsed or continuous electromagnetic radiation that may be reflected off an object and imaged using the Doppler effect.

Figure 2:
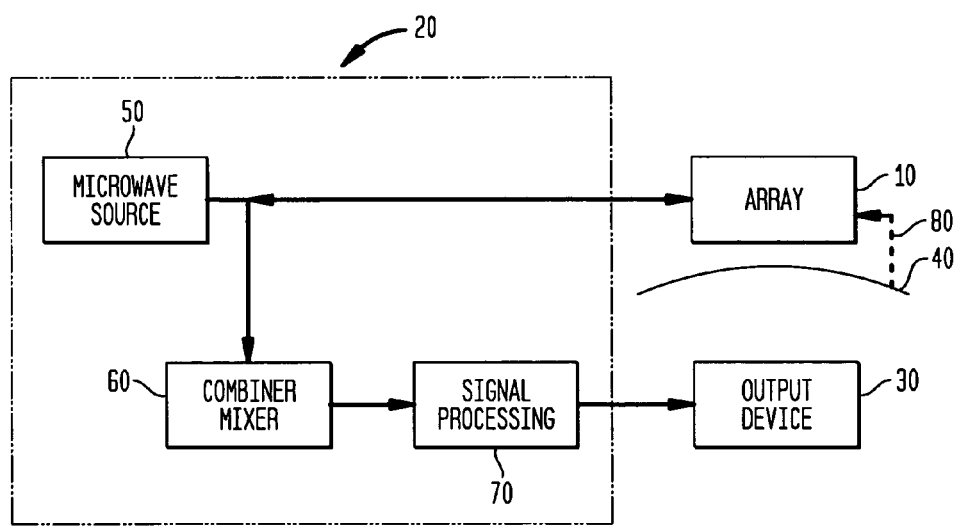
FIG. 2 illustrates a detailed block diagram of the embodiment illustrated in FIG. 1.

FIG. 2 illustrates a detailed block diagram of the embodiment illustrated in FIG. 1. As illustrated, the microwave transmit/receive device 20 incorporates a microwave source 50 that is connected to a combiner/mixer 60 and the transceiver array 10. The combiner/mixer 60 also receives an input signal 80, which will be discussed in more detail hereinafter. The combiner/mixer 60 also has an output that is connected to a signal processor 70. The signal processor 70 is connected to the output device 30.

The operation of the microwave transmit/receive device 20 in concert with the transceiver array 10 and the output device 30 will now be described. The microwave source 50 generates microwave signals that are distributed to each individual transceiver in the transceiver array 10. The signals may be the same frequency, or the signals may have differing frequencies. Microwave signals generated by the microwave transmit/receive device 20 are also provided to the combiner/mixer 60. The signals supplied by the microwave source 50 are transmitted by the individual transceivers of the transmitter array 10 into the subject 40. These transmitted signals reflect off of objects situated within the subject 40, and in particular the beating heart. These reflected signals are received by the combiner/mixer 60 as the input signal 80 via the individual transceiver probes in the transceiver array 10. The individual reflected signals are combined with the reference microwave signal received from the microwave source 50 in the combiner/mixer 60. These individual combined signals are then sent to the signal processor device 70.

It is in the signal processor 70 where the Doppler effect is used in order to create a plot of an object within the subject 40. If the signals transmitted by the transmitter array 10 reflect off of a moving object within the subject 40, then the signals that are reflected will either be higher in frequency if the object is moving closer to the transmitter array 10 or lower in frequency if the object is moving away from the array 10. The output from the combiner/mixer 60 to the signal processor is a difference between the reference microwave signal received from the microwave source 50 and the individual reflected signals received after reflection off of the object(s) within the subject 40. The signal processor 70 plots the signal differences with respect to each individual transceiver probe in the transceiver array 10 and sends the plot to the output device 30 to create an image of the moving object(s).

In one embodiment according to the present invention, the output device 30 is a cathode ray tube (CRT) or a liquid crystal display (LCD). Each individual transceiver in the transceiver array 10 is associated with a group of pixels in the output device 30. Therefore, if a signal transmitted from the array 10 undergoes a frequency change when it reflects off of an object within the subject 40, then those particular pixels associated with the individual transceiver are modified and displayed on the output device 30. For example, the pixels may be grayed or changed in color in accordance with the type of output device 30 used. The combination of pixels modified (grayed, shaded or colored) on the output device 30, in accordance with the individual transceivers of the transceiver array 10 that produce a reflected signal having a modified frequency, produce a two-dimensional image of the object moving within the subject 40. One application of this two-dimensional image is determining the size of the moving object within the subject 40.

Figure 3:
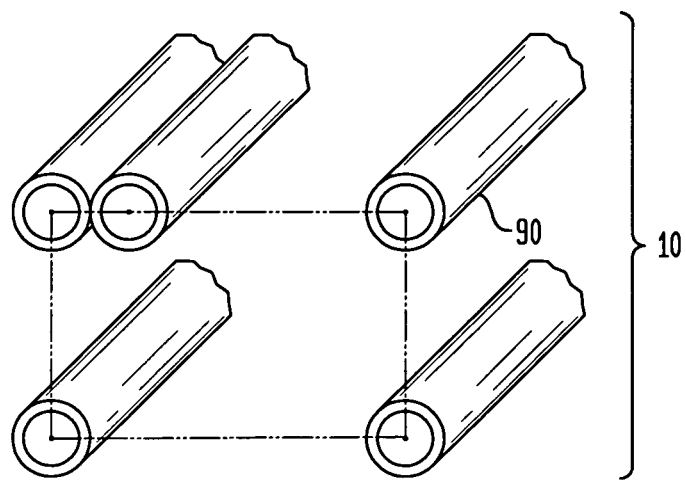
FIG. 3 illustrates the transceiver array employing coaxial probe elements according to an embodiment of the present invention.

FIG. 3 illustrates the transceiver array employing coaxial probe elements according to an embodiment of the present invention. In this embodiment, the transceiver array 10 is made up of a plurality of coaxial probes 90. These coaxial probes 90 are joined together in a flexible yet semi-rigid manner. In particular, the transceiver array 10 illustrated in FIG. 3 is formed such that it can cover a predetermined portion of the subject 40. In the embodiment illustrated in FIG. 1, this is the upper torso of the subject 40. However, other parts of the body may also be covered if desired. Moreover, other sizes and shapes of the transceiver array 10 may be used as application requirements dictate.

Each of the coaxial probes of the transceiver array 10 illustrated in FIG. 3 receives a microwave signal from the microwave transmit/receive device 20. Alternatively, it is possible that each of the coaxial probes 90 of the transceiver array 10 may incorporate its own signal source. In such an example, the microwave transmit/receive device 20 may be eliminated in favor of a transceiver array 10 that is essentially embodied as a standalone device. In particular, in this case, the transceiver array 10 only requires an interface for connecting the output device 30 thereto. Of course, each individual transceiver of the coaxial probes 90 would include a combiner/mixer 60 and a signal processor 70 for processing output to the output device 30.

Figure 4:
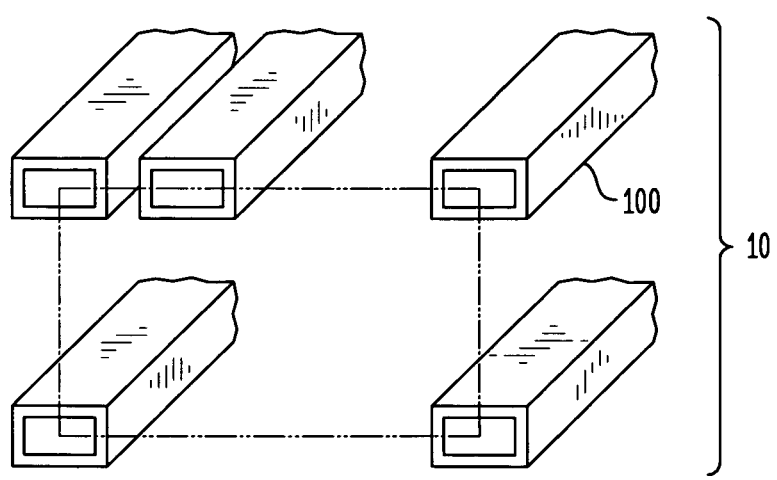
FIG. 4 illustrates the transceiver array embodied using waveguide probes according to an embodiment of the present invention.

FIG. 4 illustrates the transceiver array embodied using waveguide probes according to an embodiment of the present invention. Waveguide probes 100 operate in the same manner as discussed in relation to the coaxial probes 90 illustrated in FIG. 3. Therefore, for brevity, this description will not be repeated.

Figure 6A:
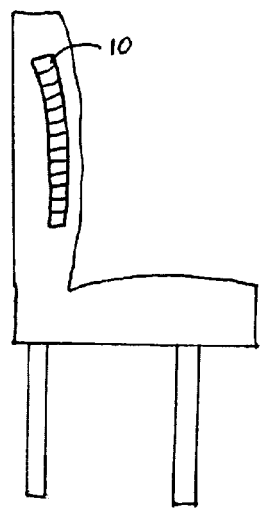
FIGS. 6A and 6B illustrate additional embodiments.
Figure 6B:
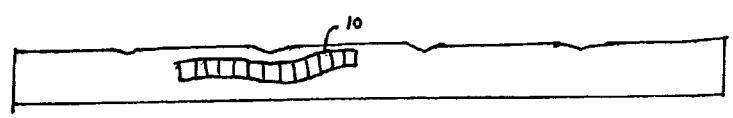

Although the embodiments of the present invention have been illustrated substantially as a transceiver array blanket that may be positioned over or on a subject, other embodiments are also possible. For example, the transceiver array 10 may be built into a table where the subject 40 simply lies thereon so that a non-invasive testing process can occur. In this case, the transceiver probes (90, 100) would be built into the table in a flexible manner such that they conform to the contours of the subject 40. As an alternative embodiment, the transceiver array 10 may also be built into a chair, in a back portion thereof, or the like and function in the same manner as the table embodiment as shown in FIG. 6A. Still further, the transceiver array 10 may also be built into a bed mattress, or a portion of a bed structure as shown in FIG. 6B, so that when a patient is positioned on the bed non-invasive testing may occur.

Figure 5:
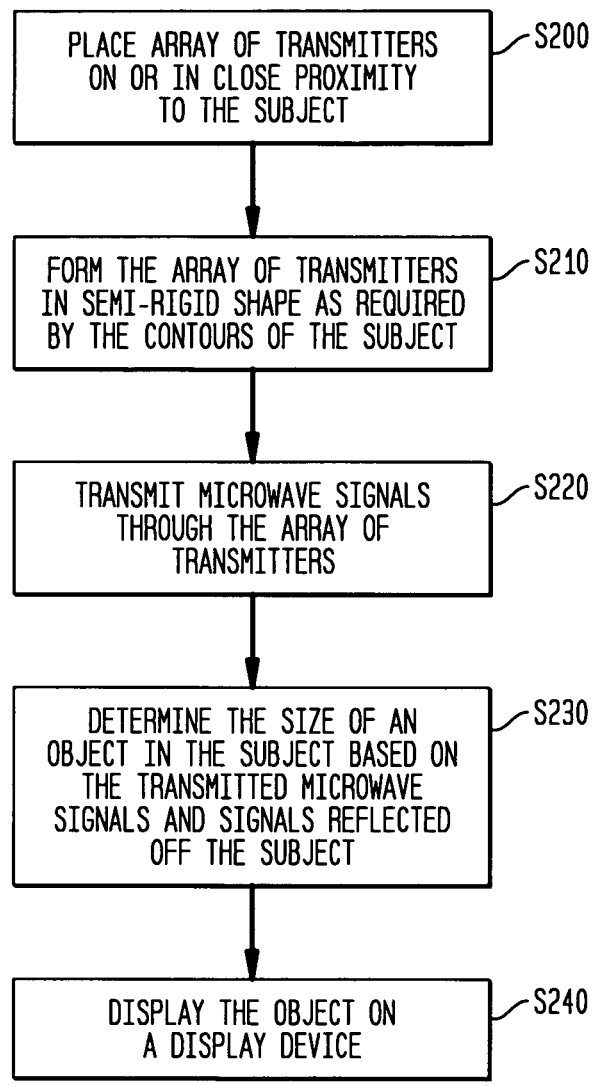
FIG. 5 illustrates a flow chart in accordance with a method of the present invention.

FIG. 5 illustrates a flow chart in accordance with a method of the present invention. First, the transceiver array 10 is positioned on or in substantially close proximity to the subject 40 (S200). The subject 40 may be either in the horizontal or standing position. Although it is advantageous to place the transceiver array 10 in direct contact with the subject 40 (over clothing or directly on skin), the transceiver array 10 can also be elevated slightly above the subject 40. Preferably, the transceiver array 10 should be in close proximity of the subject 40. Part of placing the transceiver array 10 in proximity to the subject 40 is forming the transceiver array 10 in the shape consistent with the contours of the subject 40 (S210). Due to the semi-rigid nature of the transceiver array 10, the transceiver array 10 may be positioned away from the subject 40 as required. Next, microwave signals are transmitted through the individual transceivers of the transceiver array 10 (S220). Then, using the Doppler effect, the size of an object within the subject is determined based on the transmitted microwave signals and the signals reflected off of the object (S230). In this case, the object is the beating heart. Alternatively, the size of a moving area on the surface of the subject 40 may be determined using the transceiver array 10 and the Doppler effect. These transmitted and reflected signals are coupled and mixed and associated with specific pixels of the display device 30 and displayed thereon (S240).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method of determining a characteristic of an object within a patient, comprising:
    transmitting an electromagnetic radiation signal into the patient through each of at least a plurality of signal transceivers connected together as a conformable semi-rigid unit while the conformable semi-rigid unit is spaced apart from the patient, such that the signal transceivers are moveable relative to an outer surface of the patient through which the characteristic of the object is measured;
    receiving signals reflected off of the object; and
    determining the characteristic of the object based on the reflected signals,
    wherein the electromagnetic radiation is microwave radiation.

2. The method according to claim 1, wherein a Doppler effect observed from the signals transmitted by the at least a plurality of the signal transceivers and the reflected signals are used in determining the characteristic of the object.

3. The method according to claim 1, further comprising:
    forming the conformable semi-rigid unit in a semi-rigid shape in accordance with at least one contour of the patient.

4. An object measurement apparatus, comprising:
an array of individual signal transceivers connected together as a conformable semi-rigid unit, the array of individual signal transceivers configured to measure, via electromagnetic radiation, a characteristic of an object situated within a patient while the object measurement apparatus is spaced apart from the patient, such that the signal transceivers are moveable relative to an outer surface of the patient through which the characteristic of the object is measured; and,
wherein the array is built into a bed,
wherein the electromagnetic radiation is microwave radiation.

5. An object measurement apparatus, comprising:
an array of individual signal transceivers connected together as a conformable semi-rigid unit, the array of individual signal transceivers configured to measure, via electromagnetic radiation, a characteristic of an object situated within a patient while the object measurement apparatus is spaced apart from the patient, such that the signal transceivers are moveable relative to an outer surface of the patient through which the characteristic of the object is measured, and,
wherein the array is built into of a chair,
wherein the electromagnetic radiation is microwave radiation.

6. An object measurement apparatus, comprising:
a chair having integrated therein an array of individual signal transceivers connected together as a conformable semi-rigid unit, the array of individual signal Transceivers configured to measure, via, electromagnetic radiation, a characteristic of an object situated within a patient while the object measurement apparatus is spaced apart from the subject,
wherein the electromagnetic radiation is microwave radiation.

7. An object measurement apparatus, comprising:
a conformable semi-rigid unit including an array of individual transceivers, the conformable semi-rigid unit configured to permit movement of the array of individual transceivers relative to an outer surface of a patient, and each of the individual transceivers configured to transmit an electromagnetic radiation signal and receive a reflection of the transmitted electromagnetic radiation signal; and
a processing arrangement configured to signal process output from the array of individual transceivers,
wherein the electromagnetic radiation signal is a microwave radiation signal.

8. The apparatus of claim 7, wherein the processing arrangement comprises:
a combiner configured to generate differences between the transmitted and reflected electromagnetic radiation signals; and
a signal processor configured to process the generated differences.

9. The apparatus of claim 7, wherein the signal processor is configured to plot the generated differences with respect to the individual transceivers.

\* \* \* \* \*